(12) United States Patent
Glenn, Jr.

(10) Patent No.: US 6,194,364 B1
(45) Date of Patent: Feb. 27, 2001

(54) LIQUID PERSONAL CLEANSING COMPOSITIONS WHICH CONTAIN SOLUBLE OILS AND SOLUBLE SYNTHETIC SURFACTANTS

(75) Inventor: Robert Wayne Glenn, Jr., Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/717,520

(22) Filed: Sep. 23, 1996

(51) Int. Cl.$^7$ .............................. A61K 7/50; A61K 7/48
(52) U.S. Cl. .................. 510/130; 510/159; 510/405; 510/437; 510/535
(58) Field of Search ..................... 510/130, 159, 510/405, 437, 535

(56) References Cited

U.S. PATENT DOCUMENTS

| | | | |
|---|---|---|---|
| 4,177,171 | 12/1979 | Walts | 252/541 |
| 4,515,704 | 5/1985 | Akred et al. | 252/135 |
| 5,002,688 | 3/1991 | Green et al. | 252/174.25 |
| 5,147,576 | 9/1992 | Montague et al. | 252/174 |
| 5,154,849 | 10/1992 | Visscher et al. | 252/174.25 |
| 5,753,210 | 5/1998 | McEleney et al. | 424/59 |

FOREIGN PATENT DOCUMENTS

| | | |
|---|---|---|
| 301884 | 2/1989 | (EP) . |
| 346995 | 12/1989 | (EP) . |
| 430330 | 5/1991 | (EP) . |
| 0547897 A2 | 6/1993 | (EP) . |
| 619368 | 10/1994 | (EP) . |
| 530708 | 3/1997 | (EP) . |
| 2225589 | 6/1990 | (GB) . |
| WO 91/06622 | 5/1991 | (WO) . |
| WO 91/09107 | 6/1991 | (WO) . |
| WO 91/16409 | 10/1991 | (WO) . |
| WO 94/01084 | 1/1994 | (WO) . |
| WO 94/05757 | 3/1994 | (WO) . |
| WO 94/16680 | 8/1994 | (WO) . |
| WO 95/17163 | 6/1995 | (WO) . |
| WO 96/02229 | 2/1996 | (WO) . |
| WO 96/25144 | 8/1996 | (WO) . |
| WO 97/05857 | 2/1997 | (WO) . |

*Primary Examiner*—John M. Ford
*Assistant Examiner*—Pavanaram K Sripada
(74) *Attorney, Agent, or Firm*—Tara M. Rosnell; Darryl C. Little; Andrew A Paul

(57) ABSTRACT

Liquid personal cleansing emulsion compositions which contain a moisturizing phase and an aqueous cleansing phase. The moisturizing phase comprises a nonpolar, soluble lipophilic skin moisturizing agent. The aqueous cleansing phase comprises a soluble, noncrystalline synthetic surfactant in the lamellar phase, a stabilizer and water. the liquid personal cleansing compositions here contain less than about 5% insoluble crystalline surfactant.

15 Claims, No Drawings

LIQUID PERSONAL CLEANSING COMPOSITIONS WHICH CONTAIN SOLUBLE OILS AND SOLUBLE SYNTHETIC SURFACTANTS

TECHNICAL FIELD

The present invention relates to liquid personal cleansing compositions which contain non-polar, soluble oils and soluble, noncrystalline synthetic surfactants, but which exhibit good rheology and good lathering, skin feel and stability characteristics. At least about 40% by weight of the aqueous phase is soluble noncrystalline synthetic surfactant in the lamellar phase.

BACKGROUND OF THE INVENTION

Liquid personal cleansing products are becoming more popular in the United States and around the world. Desirable liquid personal cleansing compositions must meet a number of criteria. For example, in order to be acceptable to consumers, a liquid personal cleansing product must exhibit good cleaning properties, must exhibit good lathering characteristics, must be mild to the skin (not cause drying) and preferably should even provide a moisturization benefit to the skin.

Liquid personal cleansing products which contain high levels of lipophilic skin moisturizing agents have been disclosed. In fact, consumer products, such as Oil of Olay Moisturizing Body Wash which, especially when used with the Olay Cleansing Puff, deposit lipophilic skin moisturizing agents on the skin are enormously popular with consumers. Nevertheless, some consumers would prefer to have an even greater moisturizing benefit delivered from these liquid personal cleansing products. Therefore, it would be desirable to provide a liquid personal cleansing composition with even greater moisturizing properties.

Oil of Olay Moisturizing Body Wash contains soybean oil as the lipophilic skin moisturizing agent. It has been found that superior deposition can be provided by other, more efficient, lipophilic skin moisturizing agents (e.g., petrolatum). Unfortunately, petrolatum, which contains a broad mixture of hydrocarbons, is incompatible with soluble surfactants in the isotropic micellular phase, the predominant surfactant structure employed in the liquid cleanser industry. The incompatibility stems from the solubilization of the low molecular weight hydrocarbon components of the petrolatum into the inner core of the elongated worm-like micelles where they transform the micelles from elongated aggregates to globular aggregates. This is analogous to the formation of microemulsion droplets. The net result of this transformation is rheology deterioration from the loss of elongated micelles and severe lather deterioration from the exponentially increased oil surface area (the result of surfactant binding). It has been found that oils which contain as little as 1% soluble components (e.g., petrolatum) are incompatible with soluble surfactants in the isotropic micellular phase.

In the past, the only solution to this problem was to utilize materials which, by themselves, are insoluble crystalline surfactant structures (e.g., soap) when employing nonpolar, soluble oils. See, for example, WO 94/01084 which discloses semisolid soap compositions comprising potassium C8–C22 free fatty acid soap, water, a polyol, petrolatum and C8–C22 free fatty acid and WO 96/02229 which discloses compositions comprising 5–35% C8–C22 fatty acid soap, petrolatum, and a structurant (e.g., fatty alcohols). This solution was not ideal since the insoluble crystalline surfactant imparted an unpreferred paste-like rheology in the presence of the soluble oils. Additionally, personal cleansing compositions incorporating the combination of insoluble crystalline surfactants and soluble oils tended to have stability problems and imparted an unpreferred draggy skin feel.

It has now been found, however, that liquid personal cleansing compositions which contain soluble oils or oils having soluble components, such as petrolatum, and soluble, non-crystalline synthetic surfactants and which exhibit good rheology, stability, skin feel and lathering characteristics can be obtained by manipulating the surfactant structure from the predominant and widely used micellular phase toward lamellar liquid structure, also known as the neat phase.

SUMMARY OF THE INVENTION

The present invention relates to liquid personal cleansing emulsion compositions which contain a moisturizing phase and an aqueous cleansing phase. The moisturizing phase comprises a non-polar, soluble lipophilic skin moisturizing agent. The aqueous cleansing phase comprises a lathering, soluble, noncrystalline synthetic surfactant, a stabilizer and water. At least about 40% by volume of the aqueous phase comprises soluble non crystalline synthetic surfactant is in the lamellar phase. The liquid personal cleansing compositions of the present invention contain less than 5% insoluble crystalline surfactant.

DETAILED DESCRIPTION OF THE INVENTION

The present invention relates to liquid personal cleansing compositions which provide clinically efficacious moisturization to the skin and which exhibit desirable rheology, lathering characteristics, stability and skin feel. As used herein, "liquid personal cleansing compositions" refers to rinse-off personal cleansing products, including, but not limited to, shower washes, liquid hand washes, and shampoos. The liquid personal cleansing compositions of the present invention are emulsions which contain a moisturizing phase comprising a non-polar, soluble lipophilic skin moisturizing agent and an aqueous cleansing phase comprising a lathering, soluble, noncrystalline synthetic surfactant in the lamellar phase, a stabilizer and water. The liquid personal cleansing compositions of the present invention contain less than 5% insoluble crystalline surfactant. As used herein "insoluble crystalline surfactant" refers to materials which are insoluble and crystalline at a concentration of 10% in water. Soap is an example of an insoluble crystalline surfactants.

The liquid personal cleansing compositions of the present invention, including the materials contained therein and processes for preparing, are described in detail as follows:

I. Ingredients

A. Moisturizing Phase

The liquid personal cleansing emulsion compositions of the present invention comprise a moisturizing phase which comprises from about 1% to about 30%, preferably from about 3% to about 25%, more preferably from about 5% to about 25% by weight of the composition of a non-polar, soluble lipophilic skin moisturizing agent. As used herein, the term "non-polar, soluble lipophilic skin moisturizing agent" refers to those lipophilic skin moisturizing agents which contain at least 1% by weight of soluble components. Soluble components are components which have a transmittance of greater than 5% (or greater than 3% over storage transmittance), as measured by the Turbidity Method set forth hereinafter in the Analytical Methods Section.

Suitable non-polar, soluble lipophilic skin moisturizing agent for use in the present invention include, for example, low molecular weight hydrocarbons, polymeric oils and silicones, and triglycerides comprised of predominantly short chain length fatty acids (e.g., <C1 8). Specific examples of non-polar, soluble lipophilic skin moisturizing agents for use in the personal cleansing compositions herein include petrolatum, mineral oil, coconut oil, palm oil, avocado oil, castor oil, polybutenes having a molecular weight of less than about 600, and silicones having a viscosity of less than about 1000 centistoke. Petrolatum is especially preferred for use herein.

B. Aqueous Cleansing Phase

The liquid personal cleansing emulsion compositions of the present invention also comprise an aqueous cleansing phase which comprises a lathering, soluble, noncrystalline synthetic surfactant in the lamellar phase, a stabilizer and water. Each of these is described in detail as follows:

1. THE LATHERING SURFACTANT

The personal cleansing emulsion compositions of the present invention also comprises from about 5% to about 30%, preferably from about 5% to about 25%, more preferably from about 10% to about 25%, and most preferably from about 12% to about 25% of a lathering, soluble, noncrystalline synthetic surfactant. A lathering surfactant is defined herein as a surfactant or surfactant mixture thereof that when combined have an equilibrium surface tension of between 15 and 50 dynes/cm, more preferably between 25 and 40 dynes/cm as measured at the CMC (critical micelle concentration) at 250 C. Some surfactant mixes can have a surface tension lower than those of its individual components.

The soluble, noncrystalline synthetic surfactant is selected from the group consisting of anionic surfactants; nonionic surfactants, cationic surfactants, amphoteric surfactants, and mixtures thereof.

Anionic surfactants useful herein include: acyl isethionates, acyl sarcosinates, alkylglycerylether sulfonates, alkyl sulfates, alkyl sulfates, acyl lactylate, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters,, alpha olefin sulphates, the alkyl ether sulfates (with 1 to 12 ethoxy groups) and mixtures thereof, wherein said surfactants contain C8 to C22 alkyl chains and wherein the counterion is selected from the group consisting of: Na, K, $NH_4$, $N(CH_2CH_2OH)_3$. The anionic surfactant is more preferred when selected from the group consisting of acyl isethionate, acyl sarcosinates, acyl lactylates, alkyl sulfosuccinates, alkylglycerylether sulfonates, methylacyl taurates, alkyl ether sulfates, alkyl sulfates, alkyl phosphate esters and mixtures thereof, wherein said surfactants contain has C8 to C14 alkyl chains and is present at a level of from about 8% to about 20%.

Amphoteric synthetic surfactants cannot serve as the sole surfactant in this product, but are preferred as a co-surfactant at a lower level of from about 1% to about 10%, by weight and the more preferred types are selected from alkyl-ampho mono- and di-acetates, alkyl betaines, alkyl dimethyl amine oxides, alkyl sultaines, alkyl amidopropyl betaines, alkyl amidopropyl hydroxysultaines, and mixtures thereof, wherein said surfactants contain C8 to C22 alkyl chains.

Nonionic synthetic surfactant cannot serve as the sole surfactant in this product, but can be used as a co-surfactant at a lower level of from about 1% to about 15% by weight. The more preferred types selected from the group consisting: alkyl glucose amides, alkyl glucose esters, polyoxyethylene amides, fatty alkane amides, alkyl amine oxides, alkyl polyglucosides, polyoxy ethylene alkyl phenols, polyoxyethylene esters of fatty acids, EO/PO block co-polymers such as polyoxamines and poloxamers, sorbitan esters and alcohol esters, and mixtures thereof.

Cationic synthetic surfactant cannot serve as the sole surfactant in this product, but are preferred as a co-surfactant at a lower level of from about 0.5% to about 6%, by weight. The more preferred types of cationic surfactants are selected from the group consisting: alkyl trimonium chloride and methosulfate, and dialkyldimonium chloride and methyl sulphate, and alkyl alkonium chloride and methyl sulphate and mixtures thereof. These surfactants contain C12 to C24 carbon atoms per alkyl chain. The most preferred cationic is selected from the group consisting of stearalkonium chloride, stearyltrimonium chloride, Di-stearyl-dimonium chloride, and mixtures thereof. Cationic surfactants may also act as a lipid deposition aid.

At least about 40%, preferably at least about 50%, more preferably at least about 60% and most preferably at least about 70% by volume of the aqueous phase of the personal cleansing compositions herein is comprised of soluble, noncrystalline synthetic surfactant in the lamellar (e.g., neat) phase.

A surfactant can be manipulated into the lamellar phase by a variety of known methods. See, for example, WO 96102229, herein incorporated by reference, which discloses ways to cause the surfactant to adopt the lamellar phase. Inclusion of amphoteric surfactant, structurants, electrolytes and mixtures thereof into the personal cleansing composition have been taught to cause the surfactant to adopt the lamellar phase. Structurants which cause a surfactant to adopt the lamellar phase include C8–C22 fatty acids, C8 to C22 fatty alcohols, swelling clays, such as laponite, cross-linked polyacrylates such as Carbopol™ (polymers available from Goodrich), and mixtures thereof. Suitable electrolytes include alkali and alkaline earth salts such as halides, ammonium salts and sulfates.

The liquid emulsions compositions herein contain less than 5%, preferably less than 4%, more preferably less than 3% and most preferably less than 2% by weight of the composition of insoluble, crystalline surfactants. Insoluble crystalline surfactants include, for example, fatty acid soap; alkyl, glyceryl ether sulfate and sodium cocoisethionate.

2. STABILIZER

The liquid personal cleansing compositions of the present invention also typically contain from about 0.1% to about 10%, preferably from about 0.25% to about 8%, more preferably from about 0.5% to about 5% of a stabilizer in the aqueous phase.

The stabilizer is used to form a crystalline stabilizing network in the emulsion that prevents the lipophilic skin moisturizer agent droplets from coalescing and phase splitting in the product. The network exhibits time dependent recovery of viscosity after shearing (e.g., thixotropy).

The stabilizers used herein are not surfactants. The stabilizers provide improved shelf and stress stability, but allow the oil-in-water emulsion to separate upon lathering, and thereby provide for increased lipid deposition onto the skin. This is particularly true when the oil-in-water cleansing emulsions of the present invention are used in conjunction with a polymeric diamond meshed sponge implement such as that described in Campagnoli; U.S. Pat. No. 5,144,744; Issued Sep. 8, 1992, herein incorporated by reference.

In one embodiment of the present invention, the stabilizer employed in the personal cleansing compositions herein comprises a crystalline, hydroxyl-containing stabilizer. This stabilizer can be a hydroxyl-containing fatty acid, fatty ester or fatty soap water-insoluble wax-like substance or the like.

The crystalline, hydroxy-containing stabilizer is selected from the group consisting of:

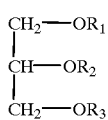

(i)

wherein
R$_1$ is

R$_2$ is R$_1$ or H
R$_3$ is R$_1$ or H
R$_4$ is C$_{0-20}$ Alkyl
R$_5$ is C$_{0-20}$ Alkyl,
R$_6$ is C$_{0-20}$ Alkyl
R$_4$+R$_5$+R$_6$=C$_{10-22}$
and wherein $1 \leq x+y \leq 4$;

(ii)

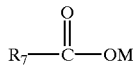

wherein
R$_7$ is —R$_4$(CHOH)$_x$R$_5$(CHOH)$_y$R$_6$
M is Na$^+$, K$^+$ or Mg$^{++}$, or H; and
iii) mixtures thereof;

Some preferred hydroxyl-containing stabilizers include 12-hydroxystearic acid, 9,10-dihydroxystearic acid, tri-9, 10-dihydroxystearin and tri-12-hydroxystearin (hydrogenated castor oil is mostly tri-12-hydroxystearin). Tri-12-hydroxystearin is most preferred for use in the emulsion compositions herein.

When these crystalline, hydroxyl-containing stabilizers are utilized in the personal cleansing compositions herein, they are typically present at from about 0.5% to 10%, preferably from 0.75% to 8%, more preferably from 1.25% to about 5% of the liquid personal cleansing compositions. The stabilizer is insoluble in water under ambient to near ambient conditions.

Alternatively, the stabilizer employed in the personal cleansing compositions herein can comprise a polymeric thickener. When polymeric thickeners as the stabilizer in the personal cleansing compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000, anionic cationic and nonionic homopolymers derived from acrylic and/or methacrylic acid, anionic cationic and nonionic cellulose resins, cationic copolymers of dimethyldialkylammonium chloride and acrylic acid, cationic homopolymers of dimethylalkylammonium chloride, cationic polyalklyene and ethoxypolyalkylene imines, polyethylene glycol of molecular weight from 100,000 to 4,000,000, and mixtures thereof. Preferably, the polymer is selected from the group consisting of Sodium Polyacrylate, hydroxy ethyl Cellulose, Cetyl Hydroxy Ethyl Cellulose, and Polyquaternuium 10.

Another stabilizer which can be employed in the personal cleansing compositions herein are C10–C22 ethylene glycol fatty acid ester. C10–C22 ethylene glycol fatty acid esters can also desirably be employed in combination with the polymeric thickeners hereinbefore described. The ester is preferably a diester, more preferably a C14–C18 diester, most preferably ethylene glycol distearate. When C10–C22 ethylene glycol fatty acid esters are utilized as the stabilizer in the personal cleansing compositions herein, they are typically present at from about 3% to about 10%, preferably from about 5% to about 8%, more preferably from about 6% to about 8% of the personal cleansing compositions.

Another class of stabilizer which can be employed in the personal cleansing compositions of the present invention comprises dispersed amorphous silica selected from the group consisting of fumed silica and precipitated silica and mixtures thereof. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. Precipitated silicas and silica gels are generally made in aqueous solution. See, Cabot Technical Data Pamphlet TD-100 entitled "CAB-O-SIL® Untreated Fumed Silica Properties and Functions", October 1993, and Cabot Technical Dat Pamphlet TD-104 entitled "CAB-O-SIL® Fumed Silica in Cosmetic and Personal Care Products", March 1992, both of which are herein incorporated by reference.

The fumed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m./gram, most preferably greater than about 180 sq. m./gram.

When amorphous silicas are used as the stabilizer herein, they are typically included in the emulsion compositions at levels ranging from about 0.1% to about 10%, preferably from about 0.25% to about 8%, more preferably from about 0.5% to about 5%.

A fourth class of stabilizer which can be employed in the personal cleansing compositions of the present invention comprises dispersed smectite clay selected from the group consisting of bentonite and hectorite and mixtures thereof.

Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and flourine. See Merck Index, eleventh Edition, 1989, entry 4538, p. 729, which is herein incorporated by reference.

When smectite clay is employed as the stabilizer in the personal cleansing compositions of the present invention, it is typically included in amounts ranging from about 0.1% to about 10%, preferably from about 0.25% to about 8%, more preferably from about 0.5% to about 5%.

3. WATER

The moisturizing personal cleansing emulsion compositions of the present invention comprise water as an essential component. The water is typically present at a level of from about 30 parts to about 80 parts, preferably from about 40 parts to about 75 parts, and most preferably from about 40 to about 65 parts of the personal cleansing compositions of the present invention.

4. OPTIONAL INGREDIENTS

The personal cleansing compositions of the present invention can also contain a number of optional ingredients in the aqueous phase.

For example, the liquid personal cleansing compositions of the present invention can optionally include water-dispersible, gel-forming polymers. This polymer is preferably a anionic, nonionic, cationic or hydrophobically modified polymer, selected from the group consisting of cationic polysaccharides of the cationic guar gum class with molecular weights of 1,000 to 3,000,000, anionic, cationic and nonionic homopolymers derived from acrylic and/or methacrylic acid, anionic, cationic and nonionic cellulose resins; cationic copolymers of dimethyldialkylammonium chloride and acrylic acid; cationic homopolymers of dimethyldialkylammonium chloride; cationic polyalkylene and ethoxypolyalkylene imines polyethylene glycol of molecular weight from 100,00 to 4,000,000; and mixtures thereof. Preferably, the polymer is selected form the group consisting of Sodium Polyacrylate, Hydroxy Ethyl Cellulose, Cetyl Hydroxy Ethyl Cellulose, and Polyquaternium 10.

The polymer is preferably included in the compositions of the present invention at a level of from about 0.1 parts to I part, more preferably 0.1 parts to 0.5 parts. The polymers can improve the sensory feel of the lipid on skin in addition to providing product stabilization. The improved sensory feel results from reduced tackiness and greasiness and improved smoothness. It is an especially preferred embodiment to use mixture of polymers, some of which are preferred for product stabilization, some are preferred for improved sensory feel. Preferred polymers to improve sensory feel are selected from the group consisting: of polyethylene glycol, hydroxypropyl guar, guar hydroxypropyltrimonium chloride, polyquaternary 3, 5, 6, 7, 10, 11 and 24 and mixtures thereof.

Another highly preferred optional component of the present compositions are one or more humectants and solutes. A variety of humectants and solutes can be employed and can be present at a level of from about 0.5 % to about 25%, more preferably from about 3.0 % to about 20 %. The humectants and solutes are non-volatile, organic materials having a solubility of a least 5 parts in 10 parts water. A preferred water soluble, organic material is selected from the group consisting of a polyol of the structure:

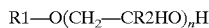

where R1=H, C1–C4 alkyl; R2=H, CH$_3$ and n=1–200; C2–C10 alkane diols; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol (including D-, L-, and the D,L-forms); pyrrolidone carboxylic acid; hyaluronic acid; lactamide monoethanolamine; acetamide monoethanolamine; urea; and ethanol amines of the general structure (HOCH$_2$CH$_2$)NH$_y$, where x=1–3; y=0–2, and x+y=3, and mixtures thereof. The most preferred polyols are selected from the group consisting of glycerine, polyoxypropylene(1) glycerol and polyoxypropylene(3) glycerol, sorbitol, butylene glycol, propylene glycol, sucrose, urea and triethanol amine.

Preferred water soluble organic material are selected from the group consisting of glycerine, polyoxypropylene (1) glycerol and polyoxypropylene (3) glycerol, sorbitol, butylene glycol, propylene glycol, sucrose, and urea and triethanolamine.

The use of oil thickening polymers, such as those listed in EP 0 547 897 A2 to Hewitt, published 23106/93, incorporated herein by reference, can also be included in the water phase of the emulsions of the present invention.

A variety of additional ingredients can be incorporated into the compositions of the present invention. These materials including, but not limited to, liquid appearance aids, salts and their hydrates and other "filler materials" are listed in U.S. Pat. No. 5,340,492, to Kacher et al., issued Aug. 23, 1994, and U.S. Pat. No. 4,919,934, to Deckner et al., issued Apr. 24, 1990; which is incorporated herein by reference.

Other non limiting examples of these additional ingredients include vitamins and derivatives thereof (e.g., ascorbic acid, vitamin E, tocopheryl acetate, and the like); sunscreens; thickening agents (e.g., polyol alkoxy ester, available as Crothix from Croda at levels up to 2% and xanthan gum at levels up to about 2%); preservatives for maintaining the anti microbial integrity of the compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), additives to impart a draggy rinse feel (e.g., fumed silica), additives to enhance deposition (e.g., maleated soybean oil at levels up to 3%), lakes, colorings, and the like (e.g., clove oil, menthol, camphor, eucalyptus oil, and eugenol).

II. Process for Preparing the Moisturizing Liquid Personal Cleansing Emulsion Compositions Herein The liquid personal cleansing compositions of the present invention can be prepared according to conventional processes. Specific, nonlimiting examples of the preparation of the personal cleansing compositions herein are set forth hereinafter in the Examples.

III. Characteristics of the Liquid Personal cleansing Compositions Herein

The liquid personal cleansing compositions of the present invention exhibit desirable rheological characteristics in spite of the inclusion of nonpolar, soluble oils as a result of utilizing surfactants in the lamellar phase. In particular, the liquid personal cleansing compositions of the present invention have a viscosity ranging from about 2,000 centipoise to about 100,000 centipoise, preferably from about 5,000 centipoise to about 70,000 poise, more preferably from about 10,000 centipoise to about 40,000 centipoise and a yield point ranging from about 5 to about 90 dynes/sq. cm., preferably from about 7 to about 50 dynes/sq. cm., more preferably from about 9 to about 40 dynes/sq. cm., and most preferably from about 11 to about 30 dynes/sq. cm., as measured by the Yield Point Method hereinafter set forth in the Analytical Methods Section..

The liquid personal cleansing compositions of the present invention also exhibit good lathering characteristics and consumer-preferred (e.g., nondraggy) skin feel and are shelf-stable.

The liquid personal cleansing compositions of the present invention also preferably provide clinically efficacious moisturization benefits to the skin. In particular, the liquid personal cleansing compositions of the present invention have a Deposition Value of at least about 10 micrograms/square centimeter, preferably at least about 15 micrograms/square centimeter, more preferably at least about 20 micrograms/square centimeter, and most preferably at least about 30 micrograms/square centimeter of lipophilic skin moisturizing agent on the skin as measured by the Deposition Method set forth hereinafter in the Analytical Methods section.

Analytical Methods

A number of parameters used to characterize elements of the present invention are quantified by particular experimental analytical procedures. Each of these procedures are described in detail as follows:

1. Viscosity of the Liquid Personal Cleansing Composition

The Wells-Brookfield Cone/Plate Model DV-II+ Viscometer is used to determine the viscosity of the liquid personal cleansing compositions herein. The determination is performed at 25° C. with the 2.4 cm° cone (Spindle CP-41) measuring system with a gap of 0.0 13 mm between the two small pins on the respective cone and plate. The measurement is performed by injecting 0.5 ml of the sample to be analyzed between the cone and plate and toating the cone at a set speed of 1 rpm. The resistance to the rotation of the one produces a torque that is proportional to the shear stress of the liquid sample. The amount of torque is read and computed by the viscometer into absolute centipoise units (mPa*s) based on geometric constants of the cone, the rate of rotation, and the stress related torque.

2. Turbidity Method for Determining Solubility of Lipophilic Skin Moisturizing Agent 1. Determine the lowest molecular weight components of the lipophilic skin moisturizing agent.
2. Prepare a solution containing the following:
   3.6% ammonium laureth-3 sulfate
   1.2% ammonium lauryl sulfate
   0.9% citric acid
   0.25% trihydroxystearin (Thixin™ from Rheox)
   4.8% sodium lauroamphoacetate (McKam IL80™ from McIntyre)
3. Heat solution to 190° F. and rapidly cool to room temperature.
4. Prepare a sample containing 0.25% lipophilic skin moisturizing agent in solution.
5. Emulsify the sample via agitation (e.g., stirrer).
6. Store at 120° F. for 24 hours.
7. Fill 0.5 inch curvette approximately ¾ full with sample.
8. Allow sufficient time for air bubble to rise out of sample (a few hours).
9. Set wavelength om Milton Roy Spectronic 20D to 580 nm.
10. Select transmittance by pushing mode button until it is highlighted.
11. Adjust readout to 0.0 (left knob).
12. Place blank sample (0 grain water) in spec. 20 and adjust readout to 100.0 (right knob).
13. Remove blank and wipe outside of curvette containing the sample with chemsipes.
14. Place sample in spec. 20, align mark on curvette with mark on spec. 20.
15. Close door and read transmittance.

3. Yield Point of Liquid Personal Cleansing Compositions

The Carrimed CSL 100 Controlled Stress Rheometer is used to determine the yield point of the liquid personal cleansing compositions. For purposes herein, the yield point is the amount of stress required to produce a strain of 1% on the liquid personal cleansing composition. The determination is performed at 77° F. with the 4 cm 2° cone measuring system set with a 51 micron gap. The determination is performed via the programmed application of a shear stress (typically from about 0.06 dynes/sq. centimeter to about 500 dynes/square centimeter) over time. If this amount of stress results in a deformation of the sample, a shear stress vs. strain curve can be created. From this curve, the yield point of the liquid personal cleansing composition can be calculated.

4. % Lamellar Phase Surfactant in Aqueous Phase
1. Prepare a sample using only aqueous phase components.
2. Pour sample into covered glass beaker and allow to equilibrate for 24 hours.
3. Lamellar phase will float and volume fraction can be measured and reported as % lamellar phase surfactant in aqueous phase.

5. Deposition of the Lipophilic Skin Moisturizing Agent
A. Preparation

The arms are washed with a nonsoap-containing, nonlipid-containing product to reduce background interference as much as possible, then blotted dry. The subject then wets the entire surface of the inner forearm with 95–100 F tap water for five seconds. The subject then saturates a puff, such as that described in Campagnoli; U.S. Pat. No. 5,144,744; Issued Sep. 8, 1992, and allows the puff to drain for 10 seconds. One milliliter of the liquid personal cleansing composition which contains the lipophilic skin moisturizing agent is applied to the forearm of the subject and then the product is rubbed with the puff for 10 seconds to generate lather. The lather is allowed to remain on the forearm for fifteen seconds, followed by a thorough rinse for fifteen seconds with the water flowing from inner elbow to wrist. The subject arm is then pat dried with a paper towel. The subject then allows the arm to "air" dry for 30 seconds.

B. Deposition Protocol-Sebumeter

Deposition of the lipophilic skin moisturizing agent on the skin is measured using a a Sebumeter SM8 10 which is commercially available from Courage and Khazaka GmbH. The Sebumeter measures the amount of lipophilic skin moisturizing agent that has been deposited on the skin via photometry of a special plastic strip, which becomes transparent when it absorbs the lipophilic skin moisturizing agent. The plastic strip is extended over a mirror which is connected to a spring. The measuring head of the device (comprised of spring, mirror and plastic strip) is pressed against the skin for 30 seconds. The Deposition Value ($\mu$g/sq. cm) is indicative of the amount of lipophilic skin moisturizing agent on the skin; the Deposition Value increases with increased amount of lipophilic skin moisturizing agent. The method is insensitive to humidity. Sebumeter readings (3) are taken along the length of the forearm and the Deposition Value ($\mu$g/sq. cm) is defined as the mean of the 3 readings, divided by a conversion factor to translate the sebumeter readings to actual deposition levels in $\mu$g/sq. cm.

The Sebumeter has the following limitations:

1. The Sebumeter tape also detects natural skin lipids. A criterion of this test is that subjects baseline value measured on the Sebumeter, prior to washing, be less than or equal to 3 µg/sq. cm of forearm skin.

2. The Sebumeter like other surface extraction measurements may not measure all the deposited lipophilic skin moisturizing agent; if the skin topography is undulating it is possible that deposited lipophilic skin moisturizing agent may not be extracted by the Sebumeter tape.

3. The Sebumeter tape becomes saturated at a Deposition Value of above about 300 µg/sq. cm; so this method can only measure deposition values up to about 300 µg/sq. cm.

4. Different lipophilic skin moisturizing agents will have different conversion factors. For testing non-petrolatum lipids, a new calibration curve is required.

C. Calibration

To translate the Sebumeter data obtained as hereinbefore described into deposition data, it is 10 necessary to generate a conversion factor. To generate the conversion factor, an extraction is done for each lipid system and the extracted sample is analyzed by gas chromatography. The extraction is done at the same time as the Sebumeter reading and is taken from the same forearm. the extraction procedure is as follows:

1) An open-ended glass cylinder (2 inches in diameter) is placed onto the subject's inner forearm and securely strapped in place.

2) Five ml of extraction solvent is added to the cylinder.

3) The liquid is stirred on the subject's arm for 30 seconds using a blunt-ended glass stirring rod. The full surface area of the enclosed forearm is treated with solvent.

4) The liquid is transferred to a 6 dram vial using a disposable transfer pipette.

5) Steps 2–5 are repeated two times (total of three samples, 15 ml of solvent collected)

The extracted sample is then analyzed by gas chromatography as follows:

| APPARATUS | |
|---|---|
| Gas Chromatograph | HP 5890 or equivalent equipped with capillary inlet system and flame ionization detector. |
| Integration System | PEN Turbochrom v4.O data system, or HP 3396 Series II integrator, or equivalent with peak-grouping capability. |
| Column | DB-5ht, 30 M × 0.32 mm I.D., 0.10 µm film thickness, J&W Scientific cat. no. 123-5731. |
| Analytical Balance | Capable of weighting to 0.0001 g. |
| Pipet | 1 mL, Class A. |
| Volumetric Flask | 1000 mL, 100 mL, glass stoppered. |
| Glass Syringe | 100 µL capacity |
| Autosampler Vials | With crimp-top caps |
| Dry Bath | Regulated at 80–85° C. |
| Pipettor | Ependorf Repeator with 12.5 mL reservoir |
| Stir Plate and Stir Bars | Teflin-coated stir bars |
| REAGENTS | |
| Heptane | ACS grade. |
| Squalane Lipid Standard GC | Aldrich cat. no. 23,431-1 or equivalent. |

| CONDITIONS | |
|---|---|
| Carrier Gas | Helium UHP grade or regular grade helium purified through a dry tube and an oxygen scrubber. Flow pressure regulated at 25 psi with 25 ml/min split. |
| Injection Mode | Splitless |
| Injection Volume | 2 µl |
| Injector Temperature | 310° C. |
| Oven Temperature Program | 100° C. for 0 minutes @ 10° C./min. to 350° C; hold for 6 min. |
| Detector Temperature | 350° C. |
| Hydrogen and Air Flows | Optimized for gas chromatograph used. |
| Bunching Factor | 2 |
| SOLUTIONS | |
| Internal Standard Solution | Into a clean, dry 100 mL volumetric flask, analytically weight 0.1 g of squalane, recording weight to nearest 0.0002 g. Dilute to volume with heptane, stopper and stir to dissolve. (A 1:1000 dilution of this solution can be used as the extraction solvent when generating samples.) |
| Lipid Stock Solution | Into a clean, dry 100 ml volumetric flask, analytically weight 0.5 gram of lipid standard, recording weight to nearest 0.0002 g. Dilute to volume with heptane, stopper and stir to mix. |
| Lipid Working Standards | Label three autosampler vials as follows: "100 µg," "300 µg" and "500 µg." Using the glass syringe, transfer 15 µL of internal standard solution into each vial. Rinse syringe well with heptane, then use it to transfer the following amounts of lipid stock solution to the vials:<br>Std.    Vol. Stock Soln. (µL)<br>100 µg   20<br>300 µg   60<br>500 µg  100<br>Dilute to approx. 0.5 mL with heptane, then cap and shake to mix. |
| OPERATION | |
| 1. Calibration | Run each standard under the above conditions. Select the 10–14 largest peaks from the calibration run and create a peak group within the calibration of the method. Assign the amount of lipid in the standard to the group for each calibration level. Plot the area ratio on the y-axis. Do not force the line through the origin or include the origin. The r2 value should be at least 0.9990. Check calibration every ten or twelve samples and at the end of the sample run. |
| 2. Sample Analysis | Evaporate samples to dryness under a stream of dry nitrogen. Reconstitute in 0.5 mL heptane. Cap tightly and place on dry bath for 5 minutes; shake to dissolve completely. Transfer to autosampler vials and analyze on calibrated instrument with the proper ISTD amount entered. Important: Because the baseline is cluttered, manually check each result file for correct peak identification. |

The GC data is then plotted on a curve versus the Sebumeter data. The slope of the curve is the conversion factor. The conversion factor for petrolatum is 0.56.

EXAMPLES

The following shower gel compositions are non-limiting examples of the liquid personal cleansing compositions of the present invention.

| Final Formula with Incorporated Complex Coascervate Premix: | #1 | #2 | #3 | #4 |
|---|---|---|---|---|
| Ammonium Lauryl Sulfate | 3.15 | 3.15 | 3.15 | 3.15 |
| Ammonium Laureth-3 Sulfate | 9.45 | 9.45 | 9.45 | 9.45 |
| Sodium Lauroamphoacetate | 5.40 | 5.40 | 5.40 | 5.40 |
| Lauryl Alcohol | 0.00 | 1.50 | 0.00 | 0.00 |
| Cetyl Alcohol | 1.50 | 0.00 | 0.00 | 0.00 |
| Lauric Acid | 0.00 | 0.00 | 1.50 | 0.00 |
| Trihydroxystearin | 0.75 | 0.75 | 0.75 | 0.75 |
| Optional Ingredients | 6.04 | 6.34 | 6.34 | 6.04 |
| Petrolatum | 16.50 | 16.50 | 16.50 | 16.5 |
| Water | QS | QS | QS | QS |
| Aqueous Phase Lamellar Structure | >60% | >50% | >50% | <20 |
| Lather (Ultimate Volume) | 500 | 450 | 500 | 300 |
| Viscosity at 120F storage for 48 hours (cp) | 16020 | 13660 | 12680 | 8060 |
| Viscosity at 120F storage for 144 hours (cp) | 15430 | 13070 | 12970 | 7077 |
| Yield Point at 120F storage for 48 hours (dynes/cm$^2$) | 14.8 | 10.0 | 8.5 | 8.1 |
| Yield Point at 120F storage for 144 hours (dynes/cm$^2$) | 12.8 | 13.2 | 9.7 | 6.2 |

What is claimed is:

1. A liquid personal cleansing composition comprising:
   A) a moisturizing phase comprising from about 1% to about 30% by weight of the composition of a non-polar, soluble lipophilic skin moisturizing agent selected from the group consisting of low molecular weight hydrocarbons, polymeric oils and silicones, and triglycerides comprised of $C_1$–$C_{18}$ fatty acids; and
   B) an aqueous cleansing phase comprising:
      1.) from about 0.1% to about 10% by weight of the composition of a stabilizer selected from the group consisting of:
         a.) crystalline, hydroxy-containing stabilizers selected from the group consisting of:

(i)

wherein
            $R_1$ is

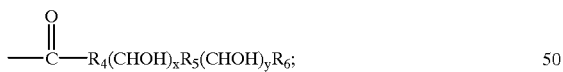

$R_2$ is $R_1$ or H
            $R_3$ is $R_1$ or H
            $R_4$ is $C_{0-20}$ Alkyl
            $R_5$ is $C_{0-20}$ Alkyl,
            $R_6$ is $C_{0-20}$ Alkyl
            $R_4+R_5+R_6=C_{10-22}$
            and wherein $1 \leq x+y \leq 4$;

(ii)

wherein
            $R_7$ is —$R_4(CHOH)_xR_5(CHOH)_yR_6$

M is $Na^+$, $K^+$ or $Mg^{++}$, or H; and
         (iii) mixtures thereof;
      b.) polymeric thickeners selected from the group consisting of anionic polymers, cationic polymers, nonionic polymers, hydrophobically modified polymers and mixtures thereof;
      c.) $C_{10-C22}$ ethylene glycol fatty acid esters
      d.) amorphous silicas;
      e.) smectite clays selected from the group consisting of bentonite, hectorite and mixtures thereof; and
      f.) mixtures thereof;
   2.) from about 5% to about 30% by weight of the composition of a lathering, soluble, noncrystalline synthetic surfactant selected from the group consisting of
      a.) anionic surfactants selected from the group consisting of acyl isethionates, acyl sarcosinates, acyl lactylates, alkyl sulfosuccinates, alkylglycerylether sulfonates, methylacyl taurates, alkyl ether sulfates, alkyl sulfates, alkyl phosphate esters and mixtures thereof, wherein said anionic surfactants comprise an anion selected from Na, K, $NH_4$ or $N(CH_2CH_2OH)_3$; and wherein the alkyl components of said anionic surfactants are from C8 to C14;
      b.) amphoteric surfactants selected from the group consisting of: alkyl-ampho-, mono- and di-acetates; alkyl betaines; alkyl dimethyl amine oxides; alkyl sultaines; alkyl amidopropyl betaines: alkyl amidopropyl hydroxysultaines: and mixtures thereof; wherein the alkyl chains of said amphoteric surfactants are from C8 to C22;
      c.) nonionic surfactants selected from the group consisting of: alkyl glucose amides, alkyl glucose esters, polyoxyethylene amides, fatty alkane amides, alkyl amine oxides, alkyl polyglucosides, polyoxy ethylene alkyl phenols, polyoxyethylene esters of fatty acids, polyoxamines, poloxamers, sorbitan esters, alcohol esters, and mixtures thereof;
      d.) cationic surfactants selected from the group consisting of: alkyl trimonium chloride and methosulfate, dialkyldimonium chloride and methyl sulphate, alkyl alkonium chloride and methyl sulphate, stearalkonium chloride, stearyltrimonium chloride, di-stearyl-dimonium chloride, and mixtures thereof;
      e.) and mixtures thereof; and
      3.) water;
wherein at least about 40% by volume of the aqueous phase is comprised of the soluble, noncrystalline synthetic surfactant in the lamellar phase; and wherein said liquid personal cleansing composition comprises less than 5% by weight of insoluble, crystalline surfactant selected from the group consisting of fatty acid soap, alkyl glyceryl ether sulfate and sodium cocoisethionate.

2. A liquid personal cleansing composition according to claim 1 wherein the stabilizer is a crystalline, hydroxyl-containing stabilizer selected from the group consisting of:

(i)

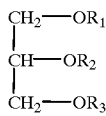

wherein

R₁ is

R₂ is R₁ or H
R₃ is R₁ or H
R₄ is $C_{0-20}$ Alkyl
R₅ is $C_{0-20}$ Alkyl,
R₆ is $C_{0-20}$ Alkyl
R₄+R₅+R6=$C_{10-22}$
and wherein $1 \leq x+y \leq 4$;

(ii)

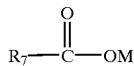

wherein
R₇ is —R₄(CHOH)ₓR₅(CHOH)R₆
M is Na⁺, K⁺ or Mg⁺⁺, or H; and
iii) mixtures thereof.

3. A liquid personal cleansing composition according to claim 2 wherein the viscosity of the liquid personal cleansing composition ranges from about 2,000 centipoise to about 100,000 centipoise.

4. A liquid personal cleansing composition according to claim 3 wherein the nonsoluble lipophilic skin moisturizing agent is selected from the group consisting of petrolatum, mineral oil, coconut oil, palm oil, avocado oil, castor oil, polybutenes having a molecular weight of less than 600, and silicones having a viscosity of less than 1000 centistokes.

5. A liquid personal cleansing emulsion composition according to claim 6 wherein the lathering, soluble, non-crystalline synthetic surfactant comprises an anionic surfactant.

6. A liquid personal cleansing composition according to claim 5 wherein at least about 70% by volume of the aqueous phase of the liquid personal cleansing composition comprises soluble, noncrystalline synthetic surfactant in the lamellar phase.

7. A liquid personal cleansing emulsion composition according to claim 6 which comprise from about 40% to about 65% water.

8. A liquid personal cleansing composition according to claim 7 which comprises from about 0.25% to about 8% of a stabilizer.

9. A liquid personal cleansing composition according to claim 8 which contains from about 12% to about 25% of the lathering, soluble noncrystalline synthetic surfactant.

10. A liquid personal cleansing composition according to claim 9 which contains less than about 2% by weight insoluble crystalline surfactant.

11. A liquid personal cleansing composition according to claim 10 which comprises from about 5% to about 25% of the nonpolar, soluble lipophilic skin moisturizing agent.

12. A liquid personal cleansing composition according to claim 11 which has a viscosity ranging from about 10,000 centipoise to about 40,000 centipoise.

13. A liquid personal cleansing composition according to claim 12 wherein the nonpolar, soluble lipophilic skin moisturizing agent is petrolatum.

14. A liquid personal cleansing composition according to claim 13 which contains from about 0.1 to about 3% of a structurant.

15. A liquid personal cleansing composition according to claim 14 wherein the structurant is selected from the group consisting of fatty acid or fatty alcohol.

* * * * *